(12) United States Patent
Bosio et al.

(10) Patent No.: US 11,298,160 B2
(45) Date of Patent: Apr. 12, 2022

(54) INTERSPINOUS FUSION DEVICE

(71) Applicants: TECHLAMED S.R.L., Florence (IT); GRUPPO SCIENZIA MACHINALE S.R.L., Pisa (IT)

(72) Inventors: Luca Bosio, Pisa (IT); Luca Ferretti, Pisa (IT); Lorenzo Fortuna, Pelago (IT); Gianni Garlatti, San Casciano Val Pesa (IT); Renzo Valleggi, Pontedera (IT)

(73) Assignee: QFUSION SPINE S.r.l., Florence (IT)

( * ) Notice: Subject to any disclaimer, the term of this patent is extended or adjusted under 35 U.S.C. 154(b) by 0 days.

(21) Appl. No.: 16/982,452

(22) PCT Filed: Mar. 25, 2019

(86) PCT No.: PCT/IB2019/052415
§ 371 (c)(1),
(2) Date: Sep. 18, 2020

(87) PCT Pub. No.: WO2019/180689
PCT Pub. Date: Sep. 26, 2019

(65) Prior Publication Data
US 2021/0077157 A1 Mar. 18, 2021

(30) Foreign Application Priority Data
Mar. 23, 2018 (IT) .................... 102018000003973

(51) Int. Cl.
*A61B 17/70* (2006.01)
(52) U.S. Cl.
CPC ...... *A61B 17/7064* (2013.01); *A61B 17/7065* (2013.01)

(58) Field of Classification Search
CPC .................. A61B 17/70; A61B 17/7062–707
See application file for complete search history.

(56) References Cited

U.S. PATENT DOCUMENTS 7,959,652 B2 * 6/2011 Zucherman ........ A61B 17/7068
606/249
8,142,479 B2 3/2012 Hess
(Continued)

FOREIGN PATENT DOCUMENTS

EP 1 982 664 A1 10/2008
WO 2007/111979 A2 10/2007
(Continued)

*Primary Examiner* — Eduardo C Robert
*Assistant Examiner* — Michelle C Eckman
(74) *Attorney, Agent, or Firm* — Maschoff Brennan

(57) ABSTRACT

An interspinous fusion device includes a central body defining a longitudinal direction and configured to be inserted between two adjacent spinous processes; and a proximal body and a distal body, opposite to each other with respect to the central body and configured to relatively translate towards each other along the longitudinal direction. A pair of proximal jaws and a pair of distal jaws opposite to each other with respect to the central body are spaced apart from each other along the longitudinal direction, and have a first end connected by hinges to the proximal body or to the distal body and a second end configured to abut against a spinous process. An actuation system percutaneously actuates the proximal and distal bodies to cause relative translation and rotation of the jaws about the proximal body and the distal body, thereby opening and closing the jaws.

18 Claims, 13 Drawing Sheets

(56) References Cited

U.S. PATENT DOCUMENTS

| | | | |
|---|---|---|---|
| 2007/0225807 A1 | 9/2007 | Phan et al. | |
| 2008/0108990 A1* | 5/2008 | Mitchell | A61B 17/7065 606/305 |
| 2011/0077686 A1* | 3/2011 | Mishra | A61B 17/7065 606/249 |
| 2011/0160773 A1* | 6/2011 | Aschmann | A61B 17/7065 606/249 |
| 2017/0348028 A1* | 12/2017 | Calvosa | A61B 17/7065 |

FOREIGN PATENT DOCUMENTS

| | | | |
|---|---|---|---|
| WO | 2011/141869 A1 | 11/2011 | |
| WO | WO-2011141869 A1 * | 11/2011 | A61B 17/7065 |
| WO | 2016088058 A2 | 6/2016 | |

* cited by examiner

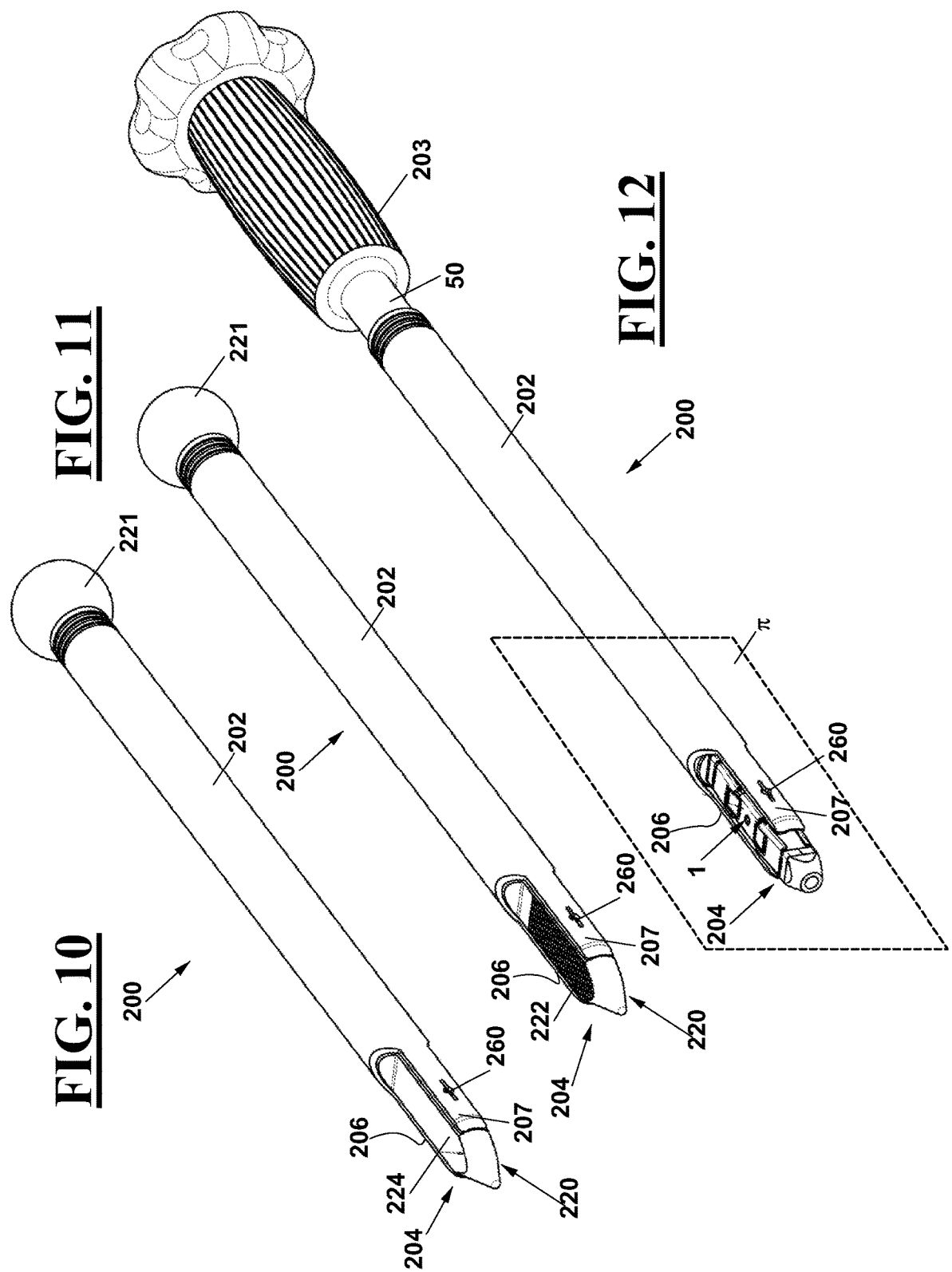

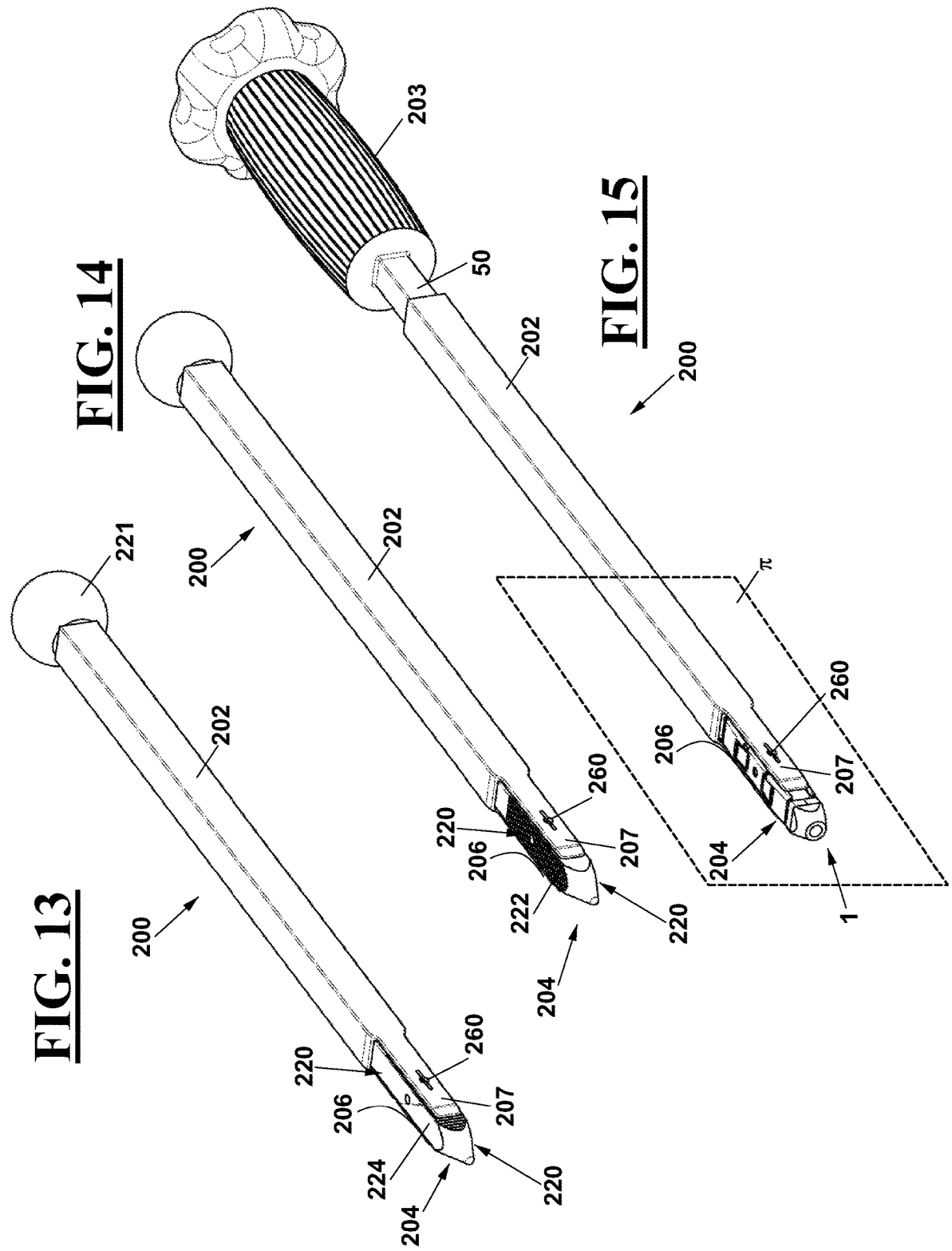

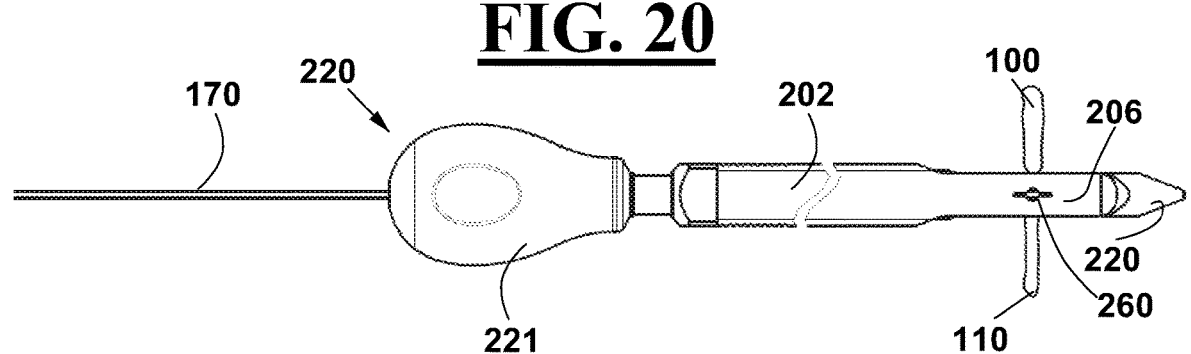
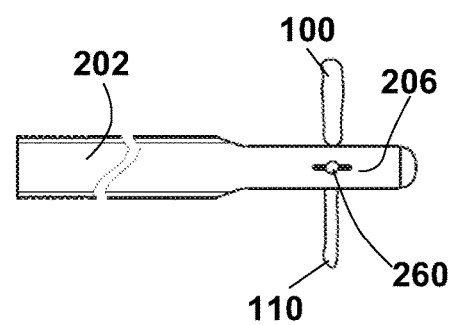
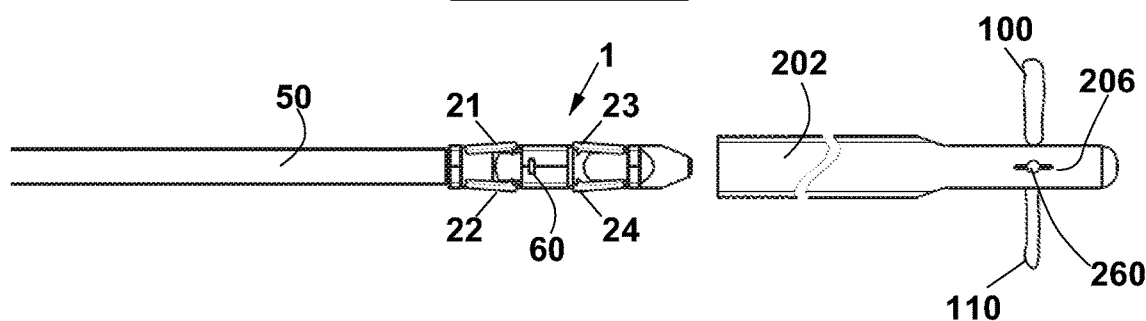
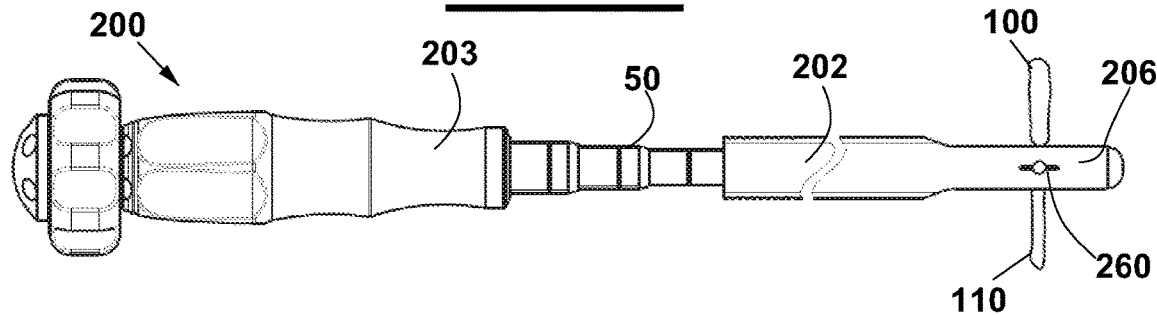

INTERSPINOUS FUSION DEVICE

FIELD OF THE INVENTION

The present invention relates to the field of intervertebral prostheses, and, in particular, the invention relates to a device configured to be implanted, percutaneously, between adjacent vertebral spinous processes of a living being, in order to fasten to each other the vertebrae in a irremovable way, obtaining a fusion or spinal fusion.

The invention comprises also a system of an interspinous fusion device and of a toolkit for its introduction in a mini-invasive way.

DESCRIPTION OF THE PRIOR ART

The devices for interspinous fusion are designed for fastening in a irremovable way to each other adjacent spinous processes of portions of a spinal column.

In particular, it is known the use of devices configured to be put in an interspinous gap by percutaneous surgical operation that, by means of couples of lateral wings configured to abut against the spinous processes, block a the relative movement of a vertebral articulation.

U.S. Pat. No. 8,142,479B2 discloses a device comprising a central body designed for percutaneous implantation and having an external screw threaded surface, in order to assist its passage and introduction between two adjacent spinous processes. The device is also provided inside of a recess arranged to house two couples of curved wings, opposite to each other with respect to a longitudinal axis of the device, and configured to rotate from a first position of minimum encumbrance, in which the two couples of wings are in the recess, to a second open position, in which the couples of wings are positioned to abut against two respective adjacent spinous processes.

However, such a device is particularly complex from a mechanical viewpoint, since it requires the use of a gearing of reduced size, which is of difficult construction and of not easy to be assembled.

WO2016088058A2 discloses a further example of a device for intervertebral distraction that can also be used for fastening to each other the vertebrae in an irremovable way. It comprises: a main body configured to be inserted between two adjacent spinous processes, two couples of proximal and distal stabilizers pivotally movable with respect to the main body and that can rotate about the respective axes and also can translate along a longitudinal direction of the main body, in order to expand and then to abut against two adjacent spinous processes. In particular, with the rotation of an actuation axis, firstly two couples opposite to jaws are opened, and then they are approached to the spinous processes, for blocking possible movement of the prosthesis.

However, such a device is particularly complex from a structural viewpoint, since it provides a gearing and it requires a high precision for mounting its components. Furthermore, when opening the jaws and approaching them to the spinous processes, a relevant part of the tissues that are present between the jaws before their closure is trapped, with high possibility of creating trauma with long reabsorption time and pain.

EP1982664A1 describes an interspinous spacer that is not conceived for carrying out an interspinous fusion, but is designed to allow a mobility. It provides in addition to a central body, a proximal body and a distal body opposite to each other with respect to the central body, and configured to translate with respect to each other along a longitudinal direction; a couple of proximal spacers and a couple of distal spacers opposite to each other are provided with respect to central body. The spacers are foldable by plastic hinges actuated by a return device that can be percutaneously actuated, for causing a translation and a relative rotation thereof from a closed configuration to an open configuration. In the open configuration, a short portion of the spacers protrudes for abutting against the spinous processes, which are contained between the spacers.

WO2007111979A2, US2007225807A2, WO2011141869A1 describe further interspinous devices that are not adapted to carry out an interspinous fusion.

SUMMARY OF THE INVENTION

It is therefore a feature of the present invention to provide an interspinous fusion device that is easy to be manufactured.

It is also a feature of the present invention to provide an interspinous fusion device that can be actuated easily.

It is another feature of the present invention to provide an interspinous fusion device comprising a very small number of parts to be assembled.

It is then a feature of the present invention to provide an interspinous fusion device by which a minimum amount of tissue is trapped between a prosthesis and spinous processes when the device is being blocked on the spinous processes.

It is still a feature of the present invention to provide an interspinous fusion device that allows a precise symmetrical movement to lock the jaws on the spinous processes.

It is also a feature of the present invention to provide an interspinous fusion device that can be more easily centered between the spinous processes.

It is a further feature of the present invention to provide an interspinous fusion device that contains firmly the spinous processes, such that a reliable fusion can be obtained.

It is then a feature of the present invention to provide an interspinous fusion device that can be introduced between the spinous processes by minimum effort.

It is also a feature of the present invention to provide a system of an interspinous fusion device and a mini-invasive implant toolkit that makes it possible to introduce the interspinous fusion device between spinous processes by minimum effort.

These and other objects are achieved by an interspinous fusion device comprising:
- a central body defining a longitudinal direction and configured to be inserted between two adjacent spinous processes;
- a proximal body and a distal body, opposite to each other with respect to the central body, configured to relatively translate towards each other along the longitudinal direction;
- a pair of proximal jaws and a pair of distal jaws opposite to each other with respect to the central body, spaced apart from each other along the longitudinal direction, and having a first end connected by hinges to the proximal body or to the distal body, respectively, and a second end configured to abut against the spinous processes;
- an actuation system configured for actuating the proximal and distal bodies, arranged to be percutaneously actuated and configured to cause the relative translation and to cause a rotation of the jaws about the proximal and distal bodies, in order to cause the jaws to move from a closed configuration to an open configuration;

connecting rods that connect the central body to the pair of proximal jaws and the pair of distal jaws, the connecting rods having a first hinge point on the central body and a second hinge point on a respective jaw.

A characterising feature of the device is that the second ends, in the closed configuration of the jaws, are arranged at a first distance from the first hinge points and at a second distance from the respective intermediate hinges, respectively, wherein the first distance is shorter than the second distance, such that, when the jaws move from the closed configuration to the open configuration, the second ends move substantially transversally to the longitudinal axis and minimize the entrapment of biological tissues between the second ends of the jaws and the spinous processes.

This way, by the action performed by the actuation system, the proximal and distal bodies become closer to each other and cause the connecting rods to be pushed against the central body. Therefore, at the beginning the connecting rods are at a head-to-head compression position between the central body and the proximal and distal bodies, and then, as the proximal and distal bodies become closer to each other and to the central body, they cause a rotation-translation movement of the proximal and distal couples of jaws towards the central body. Due to the small first distance from the first hinge points, which is shorter than the second distance from the respective intermediate hinges, the progressive raising of the jaws causes the neighboring tissues to move back, clearing the space between the jaws and the central body, such that, when the jaws eventually reach the spinous processes, the amount of tissue therebetween is very small, and the jaws steadily lock the spinous processes. The tight locking of the jaws and the reduced amount of tissues left between the jaws and the spinous processes allow the fusion to be immediately operative, which shortens the patient's convalescence.

In particular, the connecting rods and the jaws rotate oppositely to each other about the respective hinge points on the central body and on the proximal and distal bodies. This allows the second end of the jaws to substantially graze the spinous processes, enclosing therefore as less issue as possible.

Then, starting from the initial head-to-head configuration, i.e. a minimum-encumbrance configuration, which allows the device to be percutaneously inserted between two spinous processes, and in which the jaws are substantially parallel to the longitudinal direction defined by the central body, an open configuration is gradually attained, in which the first and second pair of jaws are spread apart and eventually caused to abut against the opposite faces of the two respective spinous processes. In particular, the spinous processes are eventually locked between the distal and proximal jaws.

This solution makes it possible to obtain a mechanically simple interspinous fusion device that has a minimum transversal size and that is well suited to be implanted percutaneously.

Moreover, unlike some devices described in the prior art, the device of the present invention is reliable and easy to manufacture, and does not require any complicate actuation mechanisms.

The present invention is different from WO2016088058A2, according to which the jaws abut against the spinous process starting from a first closed configuration at which they are then completely opened when they are still far from the central body, and only after opening they move towards the spinous processes. On the contrary, in the present invention, the rotation and translation movement allows the second end of the jaws to translate and at the same time to substantially graze the spinous processes, so as to enclose a minimum amount of tissues between the jaws and the spinous processes.

The present invention differs also from EP1982664A1, which does not describe a fusion device, but an interspinous spacer conceived to maintain the mobility.

Preferably, the first distance is shorter than 5 mm, more preferably it is shorter than 3 mm, even more preferably it is shorter than 1 mm. These sizes make it possible to position the end of the jaws substantially very close to the central body and, therefore, they make it possible to raise the end of the jaws from their initial position already close to the spinous processes following an optimal raising trajectory with respect to the spinous processes.

In an advantageous exemplary embodiment, the actuation system can comprise a threaded shaft configured to rotate about the longitudinal direction, the threaded shaft comprising, at a first end, a head associated with the proximal body and, at a second end, a distal nut element associated with the distal body, the head and the distal nut element configured to apply on the proximal body and on the distal body, respectively, forces that are parallel to the longitudinal direction and have opposite directions directed towards the central body, in order to cause the relative translation of the distal body towards the proximal body by the rotation of the threaded shaft.

This way, if the threaded shaft is rotated in a predetermined rotation direction by a percutaneous introduction tool configured to engage with the head of the shaft and to maintain the proximal body still, the distal nut element pulls the distal body towards the proximal body along the longitudinal direction, and causes the connecting rods to be pushed against the central body, as described above.

In particular, the distal nut element associated with the distal body is selected from the group consisting of:
- a nut element integrated in the distal body, which allows to reduce the number of assembled parts;
- a nut element external to the distal body with respect to the central body, which makes it possible to manufacture a distal body in a light material, and a distal nut element made of a tougher material and arranged to engage with the threaded shaft and to bear the compression load which is used to cause the jaws to open.

In particular, according to further advantageous exemplary embodiments of the invention, the distal nut element associated with the distal body can be selected from the group consisting of:
- a nut element comprising a flange portion external to the distal body with respect to the central body and comprising an extension portion having a nut portion arranged to engage with the threaded shaft,
- a nut element integrated in the distal body comprising an extension portion having a nut portion arranged to engage with the threaded shaft.

In both cases, the extension portion can have the nut portion arranged in a proximal position and can have a length (L) substantially equal to the translation distance covered by the threaded shaft when the jaws move from the closed configuration to the open configuration. This way, a particularly compact and axially short device is obtained, in which, in the maximally open configuration of the jaws, the second end of the screw threaded shaft does not protrude beyond the distal body, since the nut portion is in the proximal position in the extension portion, and since the screw has such a length that, in the closed configuration, the distal end is at the same height as the nut portion.

In still another advantageous exemplary embodiment of the invention, the actuation system can comprise a threaded shaft configured to rotate about the longitudinal direction, the distal body associated with a distal nut element, the central body associated with a central nut element, the distal and central nut elements configured to translate along the longitudinal direction and to cause the jaws to perform the displacement from the closed configuration to the open configuration by the rotation of the threaded shaft.

This way, the central nut element allows to separate the relative movement of the distal body towards the central body and the relative movement of the proximal body towards the central body, so that the jaws symmetrically and contemporaneously move and enclose the respective spinous processes.

In particular, the threaded shaft comprises a first threaded portion configured to engage with the central nut element, a second threaded portion configured to engage with the distal nut element, the first and second threaded portion having a ratio between the respective thread pitches (P) equal to 1:2.

By this solution the relative movement of the distal body towards the central body has the same extent and occurs at the same time as the relative movement of the proximal body towards the central body, while maintaining the central body motionless with respect to the spinous processes, and while the head of the threaded shaft advances towards the central body along with the proximal body.

According to an exemplary embodiment of the invention, the hinges and the first and second hinge points are plastic constraints made of foldable portions of material.

This solution has the advantage of providing a low-cost interspinous fusion device in which a minimum number of components is required for it to operate. Moreover, if the hinges and hinge points are manufactured as plastic hinges consisting of metal sheets portions in continuity with the jaws, the overall weight of the device is very low.

According to an advantageous exemplary embodiment of the invention, the proximal, distal and central bodies are tubular bodies.

This way, the respective central and distal nut elements, which have the function of opening the jaws, can be housed within the device, along the longitudinal direction. Moreover, the extension portion of the distal nut element can partially be engage with the central body and/or, similarly, the central nut element can partially be engage with the proximal body, which makes it possible to maximally compact the structure in the longitudinal direction of the prosthesis, even when the jaws are completely open. Furthermore, such proximal, distal and central tubular bodies can receive bone material that, once the jaws have been opened, due to the above maximally compacted configuration, can contact the spinous processes and promote osteointegration.

Advantageously, the central body, the proximal and distal bodies, the connecting rods and the proximal and distal jaws are two symmetrical halves configured to be connected along a longitudinal plane containing the longitudinal axis.

By this solution, the components can be easily manufactured and assembled. Moreover, the device can be provided starting from a thin metal sheet that is subsequently pressed and folded to provide two halves symmetrical and equal to each other, which can be connected, for instance, by welded joints along a longitudinal plane containing the longitudinal axis. In this case, also the proximal, central and distal bodies can be manufactured separately by cheap methods, such as the methods used to form nuts and screws.

Advantageously, the connecting rods have a length substantially equal to the distance between the second hinge point of the jaws and the second end of the jaws.

This solution generates, for each jaw, a substantially isosceles triangle whose oblique sides, for each jaw, are provided by the respective connecting rod by a cantilever segment between the second hinge point and the second end of the jaw. This way, during the rotation and translation movement of the jaws about the proximal and distal bodies, the second ends of the jaws translate and at the same time graze the spinous processes.

In an exemplary embodiment of the invention, the actuation system comprises a tie-rod element having an end configured to engage with the distal body, the tie-rod element configured to be pulled so as to pull the distal body towards the central body and the proximal body.

This solution makes it possible to obtain a device which can be actuated from the outside by pulling from the outside a tie-rod element arranged within the introduction toolkit and integral to the distal body, maintaining the proximal body in contact with the toolkit itself.

Advantageously, the central body of the spinal fusion device comprises a radio-opaque tag.

This way, the surgeon is enabled to determine a correct and optimal positioning of the device within the interspinous space, without using more complex radiographic devices.

Preferably, the second end of the pair of jaws can comprise an engagement means arranged to engage with a spinous process.

In particular, such an engagement means can provide sharp protrusions, which can be for instance teeth configured to penetrate in the cortical bone of the spinous processes, so as to provide a locking chain hindering a relative movement between the device and the spinous processes. As an alternative, the engagement elements can be obtained on the free end of the jaws, or can be removable engagement elements.

Advantageously, said threaded shaft or said tie-rod element are hollow, so as to allow the prosthesis to be introduced through it, for example, by means of a Kirschner wire or of any other elongated guide element.

In an advantageous exemplary embodiment, the proximal body, the central body and the distal body have a rectangular or square cross section. This makes it possible to maximize the support area for the spinous processes on the surface of the central body with respect to a circular section, which would provide a smaller support area for the spinous processes for a smaller surface. Moreover, the rectangular cross section, with respect to a circular section of the same diameter, besides providing a wider support area, requires less tissue to be spaced apart.

Preferably, the jaws are configured to move from the closed configuration to the open configuration moving in a predetermined fusion plane containing the longitudinal direction. This provides an opening movement of the jaws in the fusion plane, but not in a plane orthogonal to it, which would have occurred, instead, in the case of so-called mushroom openings.

In another aspect of the invention, the above-mentioned objects are achieved by a system of an interspinous fusion device and an introduction device, the interspinous fusion device comprising:

a central body defining a longitudinal direction and configured to be inserted between adjacent spinous processes;

a pair of proximal jaws and a pair of distal jaws that are opposite to each other with respect to the central body and are spaced apart from each other along the longitudinal direction;

an actuation system of the proximal jaws and of the distal jaws, configured to be percutaneously actuated in such a way to cause the jaws to move from a closed configuration to an open configuration, wherein, in the open configuration, the jaws have free ends abutting against the spinous processes;

wherein the jaws are configured to move from the closed configuration to the open configuration in a predetermined fusion plane containing the longitudinal direction; wherein the introduction device comprises an introduction tube configured to be inserted between two spinous processes, the introduction tube comprising a distal end, the introduction tube configured to guide the interspinous fusion device until the interspinous fusion device protrudes from the distal end of the introduction tube.

The main feature of said system is that the introduction tube comprises two stiff wings extending from the distal end, the stiff wings oriented in such a way that, when the interspinous fusion device protrudes from the distal end, the interspinous fusion device can be freely moved from the closed configuration to the open configuration in a predetermined fusion plane containing the longitudinal direction, and the stiff wings are arranged parallel to the predetermined fusion plane.

The stiff wings, already with the introduction tube firstly introduced, are firmly arranged between the spinous apophyses and keep them steadily spaced apart from each other, such that the interspinous fusion device as it is subsequently inserted, it easily enters between the spinous apophyses without requiring to be forced, until the central body is centered between the spinous apophyses in the fusion plane.

Preferably, the stiff wings have a predetermined width, and the central body has a predetermined height in the fusion plane, the width of the stiff wings substantially alike at the height of the central body, such that the stiff wings work as a spacer between two adjacent spinous processes when the interspinous fusion device is caused to protrude from the distal end.

Advantageously, the system of an interspinous fusion device and of an introduction device comprises also a file tool arranged to be slidingly received within the introduction tube and to protrude between the two stiff wings, so as to open a passageway for the interspinous device through biological tissues.

Preferably, at least the central body of the interspinous fusion device has a rectangular cross section, and the introduction tube has a rectangular cross section configured to slidingly guide the interspinous fusion device.

Preferably, the file tool has a rectangular cross section, wherein a first pair of opposite faces of the file tool comprises abrasive surfaces, whereas a second pair of opposite faces of the file tool comprises smooth surfaces.

Advantageously, the central body of the interspinous fusion device has a marker, and at least one of the stiff wings of the introduction tube has a hole, the hole arranged in such a way that, when the interspinous fusion device completely protrudes from the distal end, the marker and the hole are aligned and the marker is visible to an imaging apparatus through the hole. This solution makes it possible to easily center the interspinous fusion device with respect to the wings. For example, the marker can be fluoroscopically detectable.

BRIEF DESCRIPTION OF THE DRAWINGS

Further characteristic and/or advantages of the present invention will be made clearer with the following description of an exemplary embodiment thereof, exemplifying but not limitative, with reference to the attached drawings in which:

FIGS. 10 and 11 are two perspective views of an introduction tube of the system according to the invention, in embodiments in which a file tool is provided with smooth and abrasive surfaces;

FIG. 12 is a perspective view of the system according to the invention comprising the introduction tube as in FIGS. 10 and 11, as well as an interspinous fusion device;

FIGS. 13 and 14 are two perspective views of an introduction tube of the system according to the invention, in a further exemplary embodiment, in which both the introduction tube and the file tool have rectangular cross sections, and in which the file tool is arranged to expose two smooth faces opposite to each other or two abrasive faces opposite to each other, respectively, the abrasive adjacent to the smooth faces;

FIG. 15 is a perspective view of the system according to the invention comprising the introduction tube as in FIGS. 13 and 14 and an interspinous fusion device;

FIGS. 18-20 show steps of introduction and use of a file tool between the two spinous apophysis;

FIG. 21 shows the introduction tube of the system according to the invention, prearranged between the spinous apophyses of two adjacent vertebrae so as to receive a fusion device, in particular the fusion device according to the invention;

FIGS. 22-24 show subsequent conditions of a step of introducing a fusion device, in particular the fusion device according to the invention, into the interspinous space, by means of the introduction tube of FIG. 21;

DESCRIPTION OF SOME PREFERRED EXEMPLARY EMBODIMENTS

Figure 1:
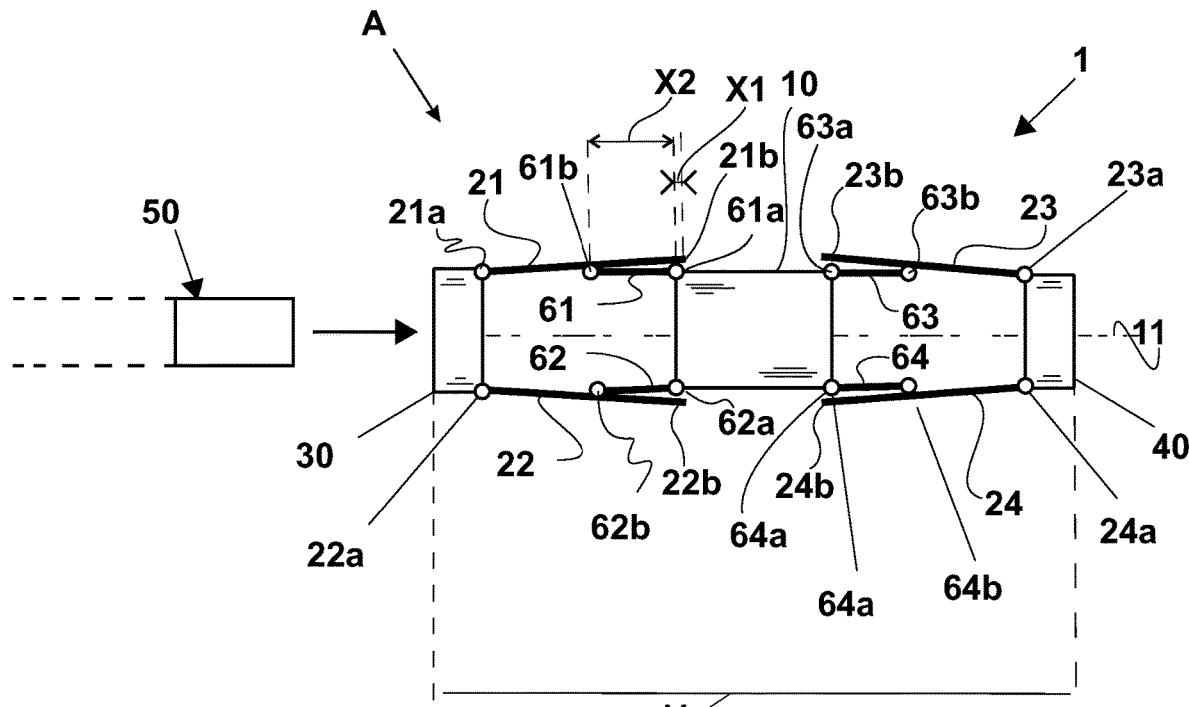
FIGS. 1,1A,1B diagrammatically show an interspinous fusion device, according to the invention, when it moves from a closed configuration to an open configuration.
Figure 1A:
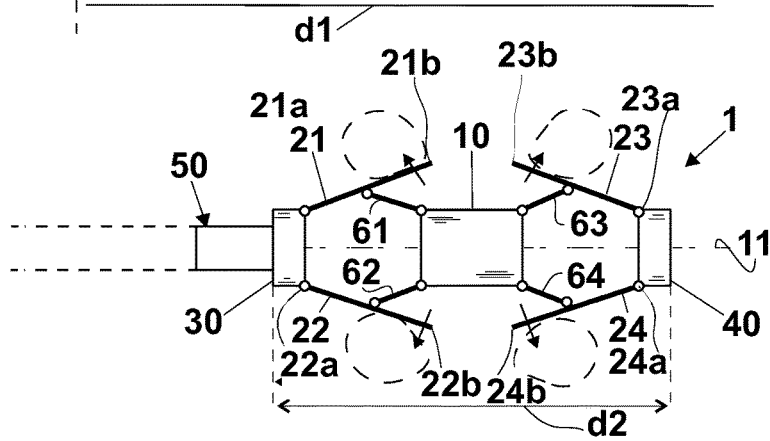
Figure 1B:
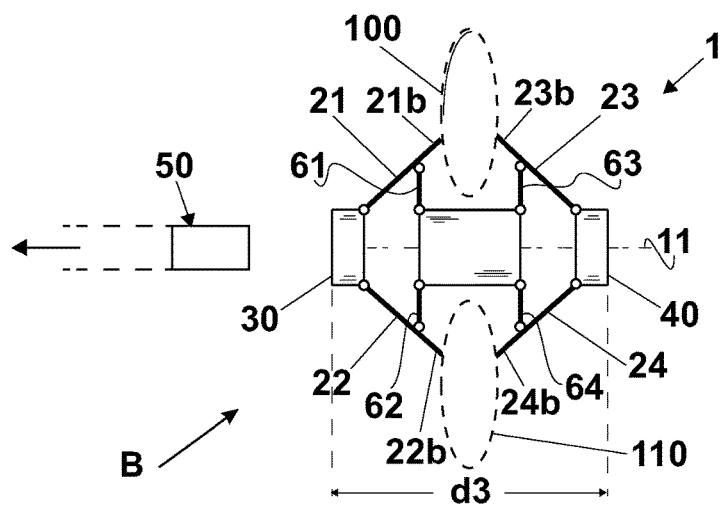

With reference to FIGS. 1,1A,1B, according to a first exemplary embodiment of the invention, a movement from a closed configuration (FIG. 1) to a second open configuration (FIG. 1B) of a device 1 for interspinous fusion according to the invention can be determined through a continuity of successive intermediate configurations, of which one is shown in FIG. 1A.

In particular, the device 1 comprises a central body 10, defining a longitudinal direction 11, and configured to be inserted between two adjacent spinous processes 100,110, indicated diagrammatically with a dashed line in FIG. 1B.

The device 1 also comprises a proximal body 30 and a distal body 40, opposite to each other with respect to central body 10, and configured to translate relatively to each other along longitudinal direction 11.

A pair of proximal jaws 21,22 and a pair of distal jaws 23,24 are provided, each jaw having a first end connected by hinges 21a,22a and 23a,24a, respectively to proximal body 30 or to distal body 40, and a second end 21b,22b,23b,24b configured to abut against a respective face of a spinous process 100,110.

In the configuration of maximum opening (FIG. 1B) the pair of proximal jaws 21,22 and the pair of distal jaws 23,24 are spread apart and approaching with one another so that the respective second ends (21b,22b,23b,24b) eventually grip two respective adjacent spinous processes 100,110. In a way here not shown advantageously, but similar to the embodiment depicted in FIGS. 5,5A,6, the second end 21b,22b,23b,24b of the couples of proximal jaws 21,22 and distal jaws 23,24 can comprise end engagement means 28 configured to grasp the respective spinous processes.

The device 1 comprises, moreover, an actuation system 50 of proximal body 30 and distal 40, configured to be percutaneously actuated, for example a tool, indicated only diagrammatically, and preferably operated by the surgeon, directly or by teleoperation, for causing the relative translation and the rotation of jaws 21,22,23,24 about proximal body 30 and distal body 40.

As shown in FIGS. 1-1B, the device 1 comprises connecting rods 61,62,63,64 that connect central body 10 to the pair of proximal jaws 21,22 and the pair of distal jaws 23,24. Connecting rods 61,62,63,64 have a first hinge point 61a, 62a,63a,64a on central body 10 and a second hinge point 61b,62b,63b,64b on a respective jaw 21,22,23,24. The hinge points can be obtained by means of pins or by means of other type of elements configured to establish a pivotal constraint between the bodies, for example, as described more in detail with reference to FIGS. 4,4A, 5,5A, 6, by means of plastic pivotal constraints made by portions of foldable material.

In particular, as shown in FIG. 1A, the gradual opening movement of jaws 21,22,23,24 can be obtained by a tool 50, which is brought to approach proximal body 30 and causes a relative approaching movement between proximal body 30, distal body 40 and central body 10, or causes separately and at the same time, a relative approaching movement between proximal body 30 and central body 10 as well as of the distal body 30 and central body 10, for example in one of the ways described hereinafter. In both cases, the relative movement of proximal body 30 and distal body 40 towards the central body causes, in turn, a pushing action of connecting rods 61,62,63,64 against central body 10.

Connecting rods 61,62,63,64 start from a substantially aligned head-to-head position (FIG. 1) of central body 10 against respect to the proximal and distal bodies, and, then, a progressive approaching movement of the proximal and distal bodies towards each other and towards central body 10, causing a rotation-translation movement of the pair of proximal jaws 21,22 and the pair of distal jaws 23,24 towards central body 10. Such rotation-translation movement is similar to that visible in FIG. 6 for another exemplary embodiment of the invention.

Figure 6:
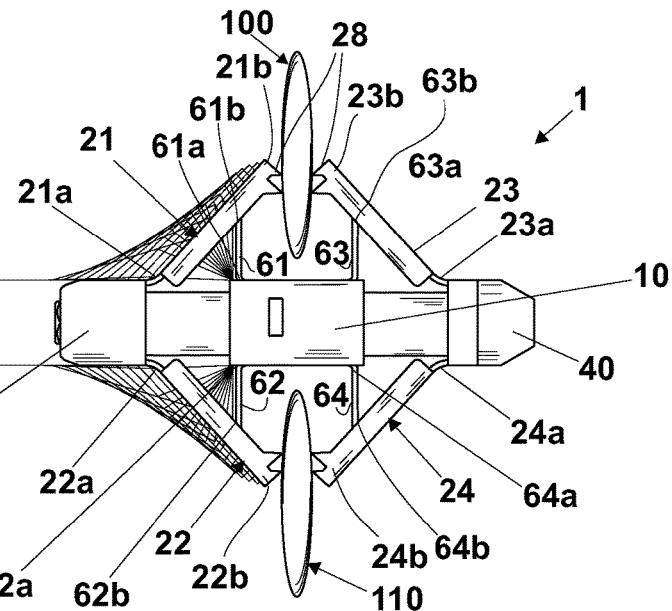
FIG. 6 diagrammatically shows an exemplary embodiment of the interspinous fusion device according to the invention, which describes the continuous rotation and translation movement of the pair of jaws in order to abut against respective spinous processes.
Figure 6A:
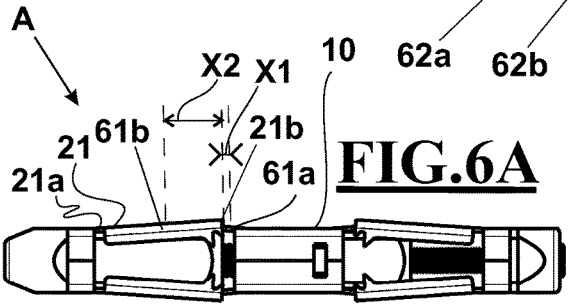
FIGS. 6A to 6F show the closed position, four intermediate progressively opening positions and the final open position.
Figure 6B:
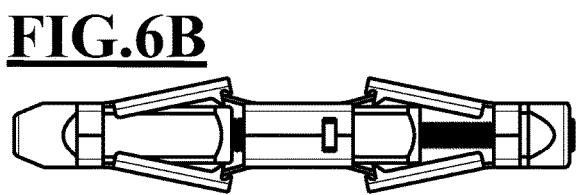
Figure 6C:
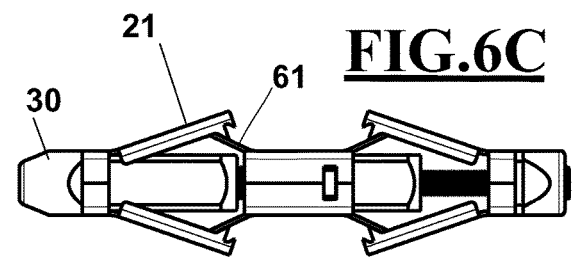
Figure 6D:
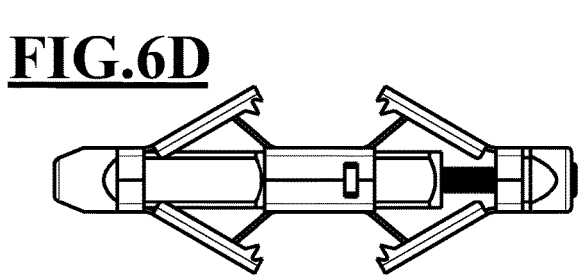
Figure 6E:
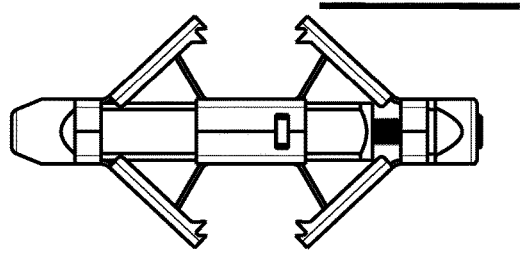
Figure 6F:
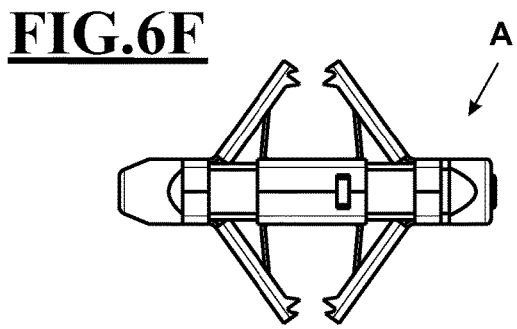

As shown by the succession of positions from FIG. 1 to FIG. 1B (and, by analogy, as shown in FIG. 6), connecting rods 61,62 and jaws 21,22 rotate opposite to each other about the respective hinge points on central body 10 and on the proximal and distal bodies. The same occurs in a symmetrically opposite way for connecting rods 63,64 and jaws 23,24. This allows the second ends 21b,22b,23b,24b of jaws 21,22,23,24 to open substantially almost grazing the spinous processes 100,110, eventually trapping, against the spinous processes 100,110 the least amount of tissues possible. In fact, the second ends 21b,22b,23b,24b of jaws 21,22,23,24 are located, already at the initial position of FIG. 1, in an axial direction with respect to axis 11, at a not significant distance from the final position that they eventually reach, in a way almost grazing the spinous processes, which then the jaws grasp inbetween.

According to the invention, said second ends 21b,22b, 23b,24b, in said closed configuration of said jaws, are arranged respectively at a first distance X1 from said first hinge points 61a,62a,63a,64a and at a second distance X2 from the respective intermediate hinges 61b,62b,63b,64b, where said first distance X1 is less than said second distance X2, such that, when said jaws 21,22,23,24 move from said closed configuration A to said open configuration B, said second ends 21b,22b,23b,24b move substantially transversal to the longitudinal axis and minimize the amount of biological tissues between the second ends 21b,22b,23b,24b and the spinous processes 100,110.

Figure 2:
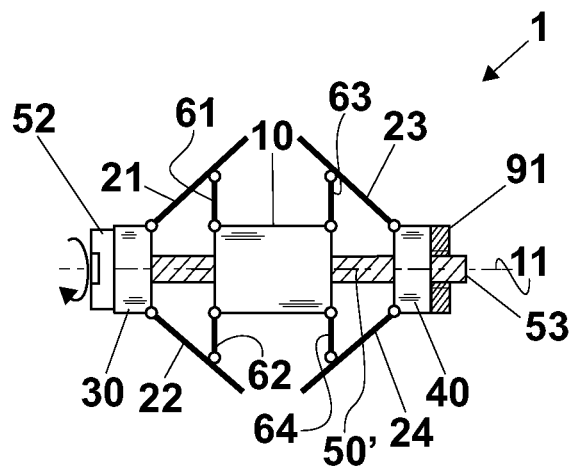
FIGS. 2,2A,2B,2C diagrammatically show respective exemplary embodiments of the interspinous fusion device according to the invention, with different exemplary embodiments of a distal nut element associated with the distal body.
Figure 2A:
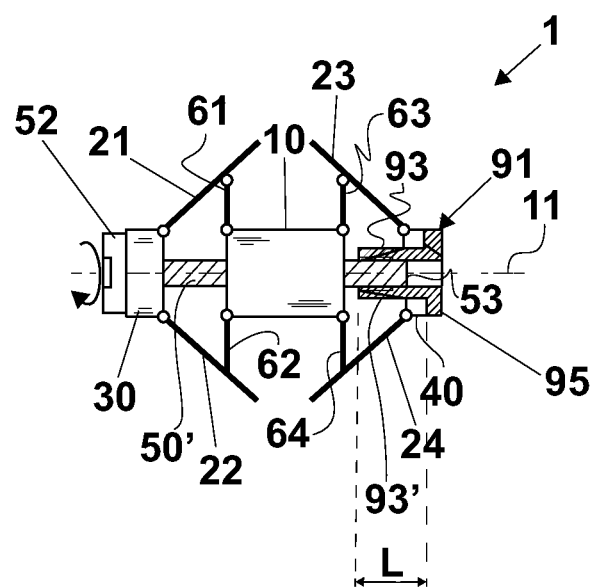
Figure 2B:
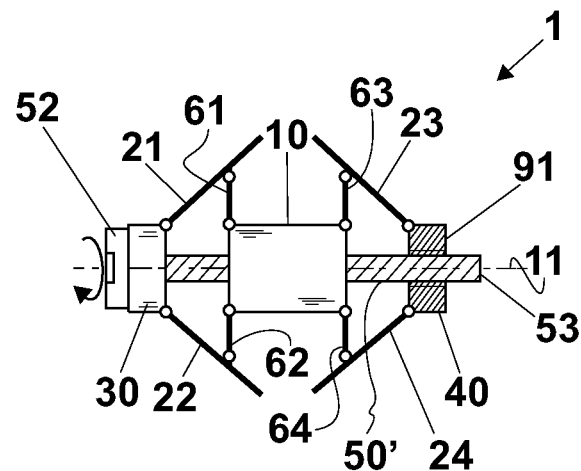
Figure 2C:
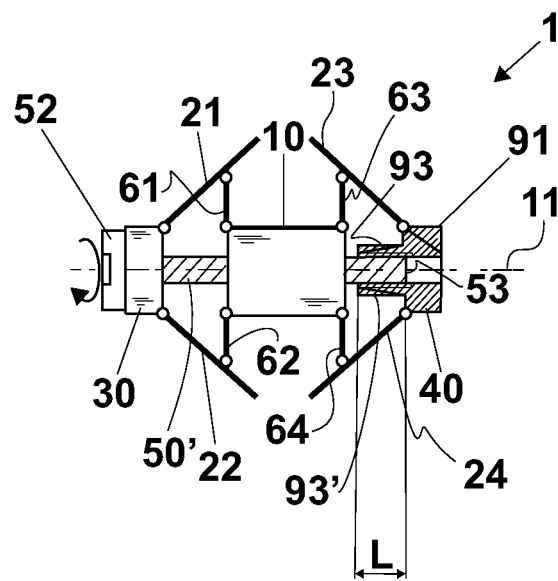

As shown in FIGS. 2-2C, according to respective exemplary embodiments of the device 1 of FIGS. 1-1B, a distal nut element 91 is provided that is associated with distal body 40 and that can be actuated by a threaded shaft 50', for engagement by actuation tool system 50, and configured to rotate about longitudinal direction 11. Threaded shaft 50' comprises, at a first end 51, a head 52, associated with proximal body 30 and, at a second end 53, a distal nut element 91 associated with distal body 40. The head 52 and distal nut element 91 are configured to apply on proximal body 30 and on distal body 40, respectively, forces that are parallel to longitudinal direction 11 and have opposite directions directed towards central body 10, in order to cause, with the rotation of threaded shaft 50', a relative translation of distal body 40 towards proximal body 30, in a similar way as described for the exemplary embodiment of FIGS. 1-1B.

As shown in an exemplary embodiment of FIG. 2, distal nut element 91 associated with distal body 40 is a nut element 91 external to distal body 40 with respect to central body 10.

In an advantageous exemplary embodiment, the nut element 91 can be a nut element (FIG. 2A) comprising a flange portion 95 external to distal body 40 with respect to central body 10, and also comprising an extension portion 93 having a nut portion 93' arranged in proximal position and configured to engage with threaded shaft 50'. The extension portion 93 has a length L substantially equal to the translational stroke of threaded shaft 50' when moving from the closed configuration to the open configuration of the pairs of jaws 21,22,23,24. This way, the length of threaded shaft 50' is minimized, and it is avoided that an end of the threaded shaft can protrude beyond distal nut element 91, in the configuration of maximum opening of the jaws. For maximizing the final stiffness of the prosthesis, the extension portion 93, when approaching along longitudinal direction 11, can protrude in part into central body 10, which is configured for allowing its free passage without generating interference.

In another exemplary embodiment, as shown in FIG. 2B, the nut element is integral with distal body 40, for example by means of inner threaded hole made in distal body 40. Such solution reduces the number of components of the prosthesis.

With reference to FIG. 2C an exemplary embodiment is shown as a variation of that of FIG. 2B, where the nut element integrated with distal body 40 has, and similarly as it is described in FIG. 2A, an extension portion 93 is provided, having a nut portion 93' in proximal position and arranged to engage with threaded shaft 50'. Similarly to FIG. 2A, the extension portion 93 has a length L substantially equal to the translational stroke of threaded shaft 50' when moving from the closed configuration to the open configuration of jaws 21,22,23,24, for achieving the same object of minimizing the length of threaded shaft 50'.

Figure 3:
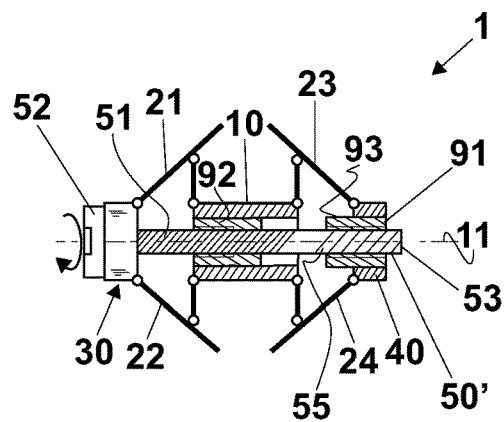
FIG. 3 shows an exemplary embodiment of the invention, comprising a threaded shaft, a distal nut element associated with the distal body and a central nut element associated with the central body, wherein the threaded shaft comprises two central and distal threaded portions, the latter having a pitch that is twice the pitch of the former.

With reference to FIG. 3, the device 1 comprises a threaded shaft 50', configured to rotate about longitudinal direction 11. Distal body 40 is associated with a distal nut element 91, central body 10 is associated with a central nut element 92. The screw nut distal element 91 and central nut element 92 are configured to translate along longitudinal direction 11 and to cause the movement from the closed configuration to the open configuration of jaws 21,22,23,24 with the rotation of threaded shaft 50'.

In particular, threaded shaft 50' comprises a first threaded portion 51 configured to engage with central nut element 92, a second threaded portion 55 configured to engage with distal nut element 91. The two threaded portions 51,55 have a ratio between the respective thread pitches (P) equal to 1:2.

Furthermore, distal nut element 91 can comprise an extension portion 93, similar to that described for the exemplary embodiments of FIGS. 2A and 2C.

Figure 4:
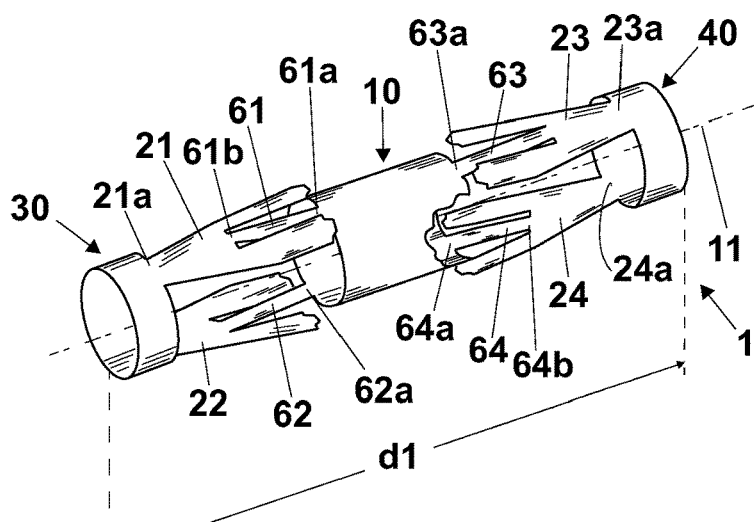
FIGS. 4,4A diagrammatically show a further exemplary embodiment of the interspinous fusion device according to the invention, comprising tubular proximal, central and distal bodies, wherein the hinges and the first and second hinge points are determined by plastic deformation.
Figure 4A:
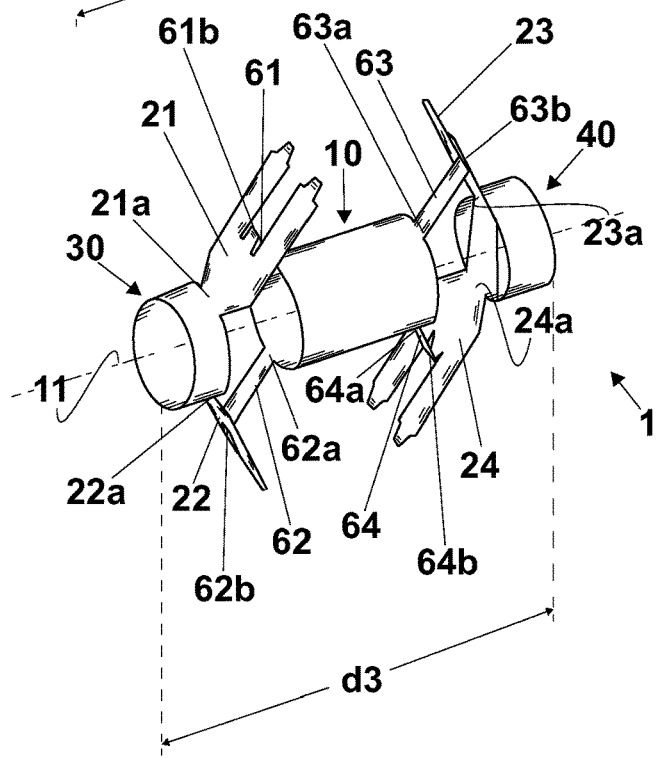

With reference to FIGS. 4,4A an example is shown of a device 1 for interspinous fusion in two respective configurations of closure and maximum opening (d1>d3). In particular, the hinges 21a,22a,23a,24a and the first and second hinge points 61a,62a,63a,64a are plastic pivotal constraints made of portions of foldable material, for example by means of metal sheet portions.

Furthermore, proximal body 30, distal body 40 and central body 10 are tubular bodies. In FIGS. 4,4A an actuation mechanism, a threaded shaft and a nut element or nut elements, or other elements used for causing the distal body to approach the central body and the proximal body are not shown for simplicity, since obtainable by a skilled person in a similar way as described here and as above described with reference to FIGS. 1 to 3.

The solution of FIGS. 4,4A provides the central, proximal and distal bodies 10,30,40 and the relative connecting rods and jaws as a single part, for example of light biocompatible metal sheet material, and then reducing to a single element, of easy construction and assembly. Its operation, even if not shown for simplicity, is obtainable for example as described relatively to FIGS. 2-2C or FIG. 3.

Figure 5:
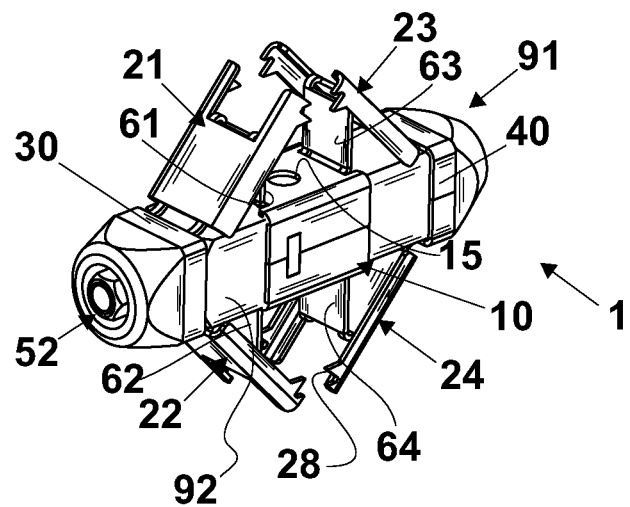
FIG. 5 shows a further exemplary embodiment of the invention wherein the proximal, distal and central bodies, as well as the proximal and distal jaws are manufactured in two halves that are connected along a plane containing the longitudinal axis.
Figure 5A:
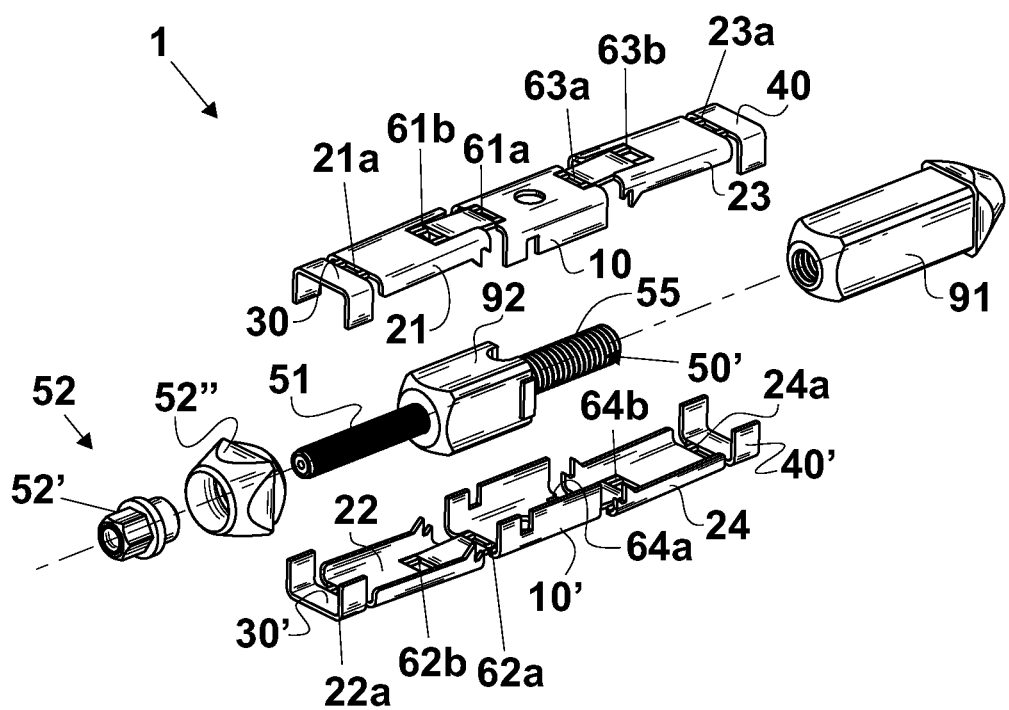
FIG. 5A shows an exploded view of FIG. 5.

With reference to FIGS. 5,5A an exemplary embodiment is shown of the device 1 of FIGS. 4, 4A, where the central body 10, proximal body 30, distal body 40, connecting rods 61,62,63,64, proximal and distal jaws 21,22,23,24 are two symmetrical halves configured to be connected along a longitudinal plane containing longitudinal direction 11. The union can be for example done by welding.

In a possible embodiment, according to FIGS. 5 and 5A, similarly to the exemplary embodiment of FIG. 3, device 1 can comprise threaded shaft 50' having two threaded portions 51 and 55 with a ratio 1:2 between the respective thread pitches P. Distal body 40 can be associated with distal nut element 91, central body 10 can be associated with central nut element 92, the head 52 can be associated with proximal body 30 and can be made as two portions 52',52". The distal nut element 91 and central nut element 92 may have square or rectangular cross section and in a similar way the central, proximal and distal bodies 10,30,40 can have, once coupled the two halves, tubular square or rectangular shape, allowing easy construction and assembly.

In particular, in a possible embodiment as shown in FIGS. 5,5A, an abutment head 52' has a screw threaded blind hole that engages first threaded portion 51 of threaded shaft 50' until becoming integral to it. This way, by an introduction toolkit, not shown in the figures and configured to engage with abutment head 52', it is possible to apply on it a torque and to cause threaded shaft 50' to rotate. This allows a movement between head portion 52" of proximal body 30 and central nut element 92, integral to central body 10, along longitudinal direction 11, causing central body 10 to approach the proximal body, and then the rotation already above described of jaws 21,22,23,24 and of connecting rods 61,62,63,64 about the respective hinge points.

Furthermore, on jaws 21,22,23,24 engagement elements 28 are provided configured to engage with respective spinous processes (also shown in FIG. 6 with 100,110) having the shape of teeth, capable of abutting thereon and penetrating in the bone material, allowing a safe fusion as well as a compliance that permits small adjustment movements before a permanent bone fusion is achieved.

The device 1 also can comprise a radio-opaque tag 15, on central body 10, arranged to assist a correct referencing of the device 1 in the interspinous space.

In particular, with reference to FIG. 6, an exemplifying interspinous fusion device 1 for is shown in an open configuration, where the pairs of jaws 21,22,23,24 are depicted in a position with engagement elements 28 abutting against the respective spinous processes 100,110.

In the figure, furthermore, a trajectory of successive positions of the pair of jaws 21,22 and of proximal body 30 when moving from the closed configuration to the open position is depicted with phantom lines.

Figure 7:
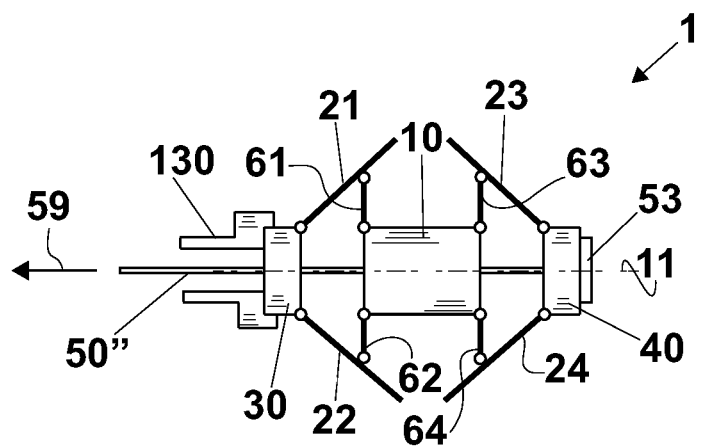
FIG. 7 diagrammatically shows an exemplary embodiment of an interspinous fusion device, according to the invention, which can be actuated by a pulling element.
Figure 8:
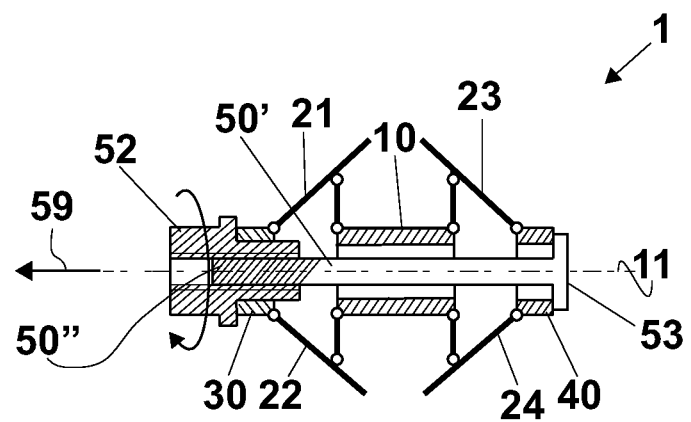
FIG. 8 diagrammatically shows an exemplary embodiment of an interspinous fusion device, according to the invention, comprising a threaded shaft with a second end in contact with the distal body and configured to apply a pulling force thereto.

With reference to FIGS. 7,8, two exemplary embodiments are respectively shown that are alternative to the previously described embodiments, concerning the actuation system. They provide an actuation system 50 comprising a tie-rod element 50" having an end 53 configured to engage with distal body 40. The tie-rod element 50" is configured to be remotely pulled so as to pull in turn distal body 40 towards central body 10 and proximal body 30.

In the exemplary embodiment of FIG. 7, device 1 is depicted actuated by a tie-rod element 50" in the example in the form of a cable. By a toolkit configured for gripping proximal body 30, a pulling force is exerted in a direction of arrow 59, in order to cause an opening movement of jaws 21,22,23,24.

In the exemplary embodiment of FIG. 8, a tie-rod toolkit can provide a threaded shaft, which engages head 52 associated with main body 30, so that, by rotating the head 52, the threaded shaft moves in a direction indicated by arrow 59, causing distal body 40 to approach central body 10 and causing central body 10 to approach proximal body 30.

Alternatively, head 52 can be replaced by a toolkit configured to engage with the threaded shaft within proximal body 30.

Figure 9:
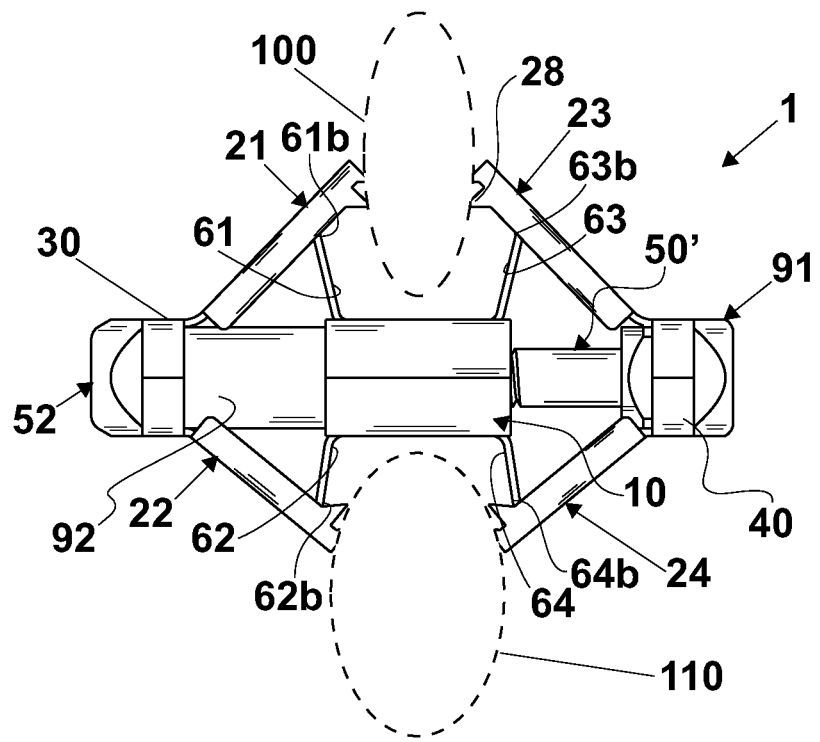
FIGS. 9 and 9A show two respective views of an exemplary embodiment of the invention, in which the interspinous fusion device comprises pairs of asymmetrical jaws comprising respective connecting rods and shorter jaws.
Figure 9A:
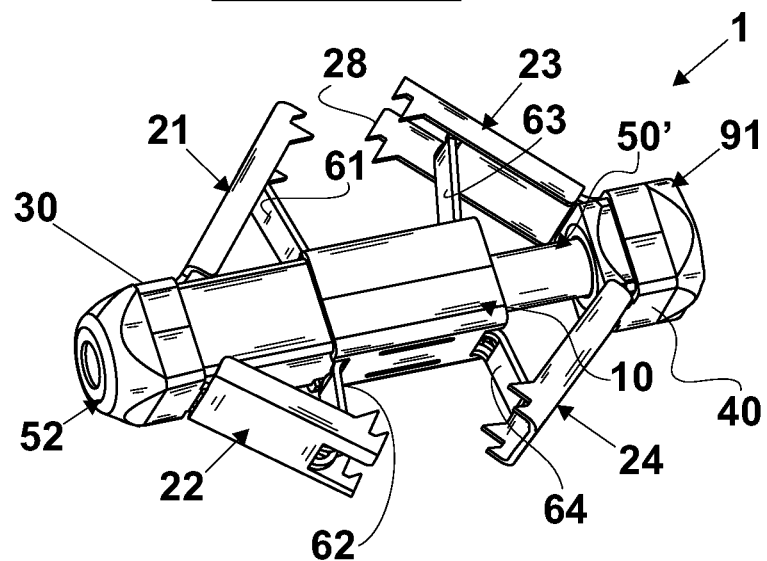

With reference to FIGS. 9-9A a possible exemplary embodiment of interspinous fusion device 1 of the invention is described, where the couples of proximal jaws 21,22 and distal jaws 23,24 are different from each other. In particular, it is possible to change the lengths of the second hinge points 61b,62b,63b,64b of connecting rods 61,62,63,64 on the respective jaws 21,22,23,24.

This solution allows applying the interspinous fusion device 1 between two vertebrae 100,110 having shape very different from each other, such as it can occur in case of application between a last lumbar vertebra (L5) and a first sacral vertebra (S1), or in the cases of deformed vertebrae.

In FIG. 12 for a circular introduction tube, and in FIG. 15 for a quadrangular introduction tube, a system of an introduction device 200 and an interspinous fusion device is shown, for example such as the one above-described above, but also of other various types having jaws that can move in the fusion plane.

The introduction device 200 comprises an introduction tube 202 configured to be inserted between two spinous processes 100,110, the introduction tube 202 comprising a distal end 204, the introduction tube 202 configured to guide the interspinous fusion device until the interspinous fusion device protrudes from the distal end 204 of the introduction tube 202.

According to the invention, the introduction tube 202 comprises two stiff wings 206,207 extending from the distal end 204. The stiff wings 206,207 are oriented in such a way that, when the interspinous fusion device protrudes from the distal end 204, it can be freely moved from the closed configuration to the open configuration B in a predetermined fusion plane 7 containing longitudinal direction 11. The stiff wings 206,207 are arranged parallel to the predetermined fusion plane π.

The introduction device 200 can advantageously provide such stiff wings 206,207 which have a predetermined width between each other and arranged to align central body 10 with a predetermined height fusion plane π, the width of the stiff wings 206,207 substantially alike the height of central body 10, in such a way that the stiff wings 206,207 work as a spacer between two adjacent spinous processes 100,110 when the interspinous fusion device is caused to protrude from distal end 204.

In a further advantageous embodiment, the introduction device 200, similar to that shown in FIGS. 10 and 11 for a circular introduction tube, and similar to that shown in FIGS. 13 and 14 for a quadrangular introduction tube, can comprise also a file tool 220 arranged to be slidingly received within the introduction tube 202 and to protrude between the two stiff wings 206,207, so as to form a passageway through biological tissues for the interspinous device. The file tool may have an end with a sharp tip configured for penetrating through the tissues and clear a passageway for the file and for the stiff wings 206,207, which are eventually stably positioned between the spinous processes.

In particular, in the embodiment of FIGS. 13 and 14, central body 10 of the interspinous fusion device has a rectangular cross section, and the introduction tube 202 has a rectangular cross section configured to slidingly guide the interspinous fusion device. In particular, the file tool 220 has a rectangular cross section, wherein a first pair of opposite faces of the file tool 220 has abrasive surfaces 222, whereas a second pair of opposite faces of the file tool 220 has smooth surfaces 224. In this case, the file is arranged to expose selectively two smooth faces opposite to each other (FIG. 13) or own abrasive faces (FIG. 14) opposite to each other and adjacent to respective smooth faces.

Advantageously, central body 10 of the interspinous fusion device has a marker 60 and at least one of the stiff wings 206,207 of the introduction tube 202 has a hole 260, the hole 260 arranged in such a way that, when the interspinous fusion device completely protrudes from the distal end 204, the marker 60 and the hole 260 are aligned, and the marker 60 is visible to an imaging apparatus through the hole 260.

Figure 16:
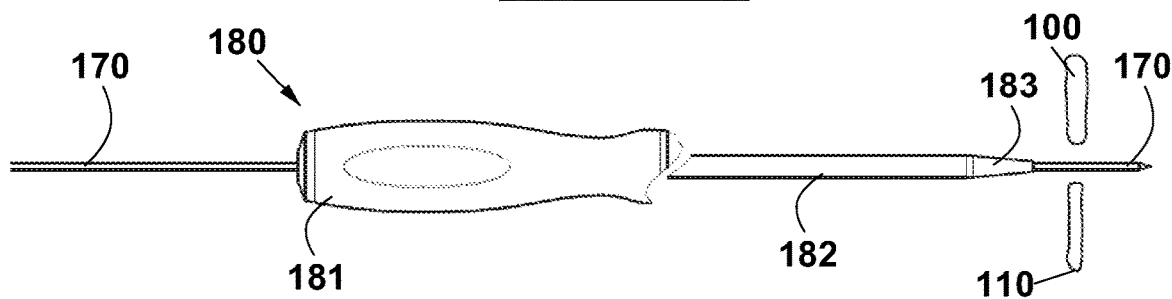
FIGS. 16 and 17 show steps of introduction and use, respectively, of a first tool to be optionally used to form a space between the tissues so as to receive the device the introduction device at once.
Figure 17:
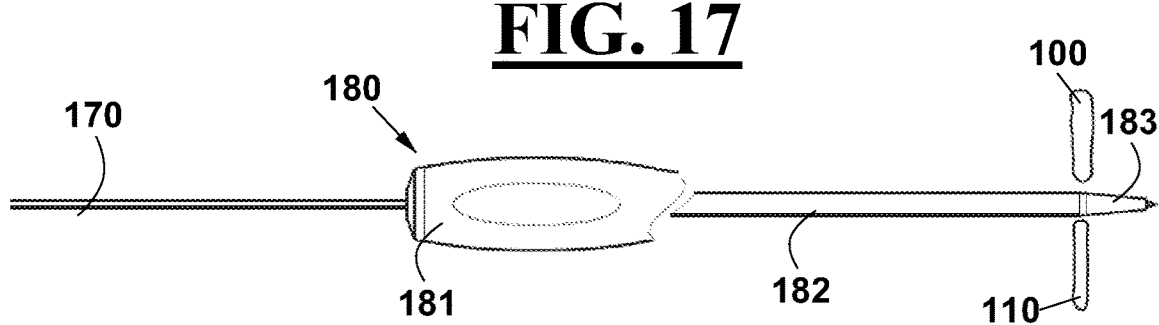

With the same reference numbers, possible introduction steps are also described: in FIGS. 16 and 17 respective steps are shown of introducing a Kirschner wire 170 and of operating a first instrument 180, which can be optionally provided, forming preliminarily between the tissues a space for receiving the device along with the introduction device, for example consisting of a knob 181, a tip 183 and a rod 182.

Figure 18:
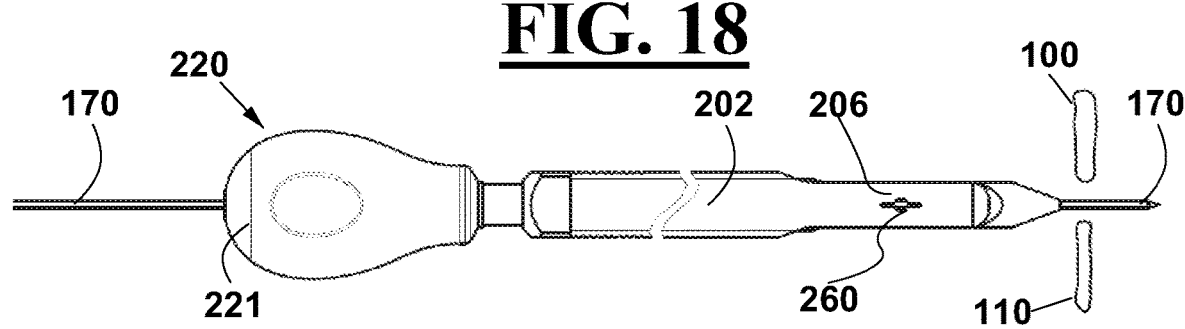
Figure 19:
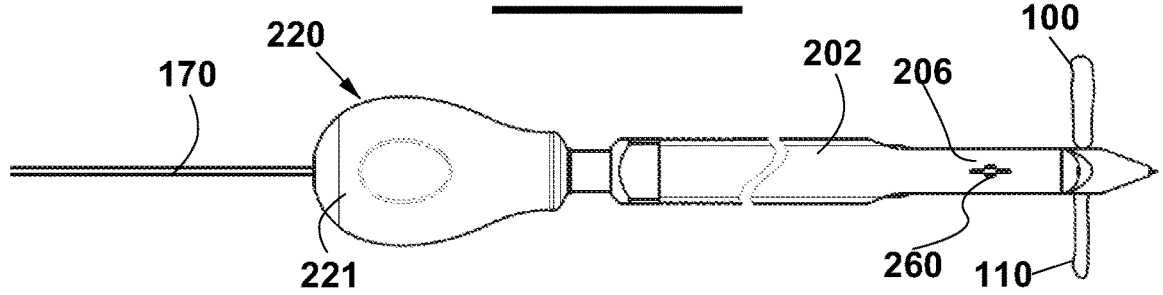

In FIGS. 18-20 show steps of introduction and operation of a file tool between two spinous apophyses, with file 220 and introduction tube 200 equipped with stiff wings 206 and 207 that are parallel to the fusion plane, the whole shown sliding along the Kirschner wire 170. The introduction is assisted with a knob 221.

As shown in FIG. 21 the introduction tube 200 of the system according to the invention, which are located between the spinous apophyses of two adjacent vertebrae for receiving a fusion device, in particular the fusion device 1 according to the above described invention. The introduction and the operation of the device 50 can be made by means of a knob 203.

Figure 24:
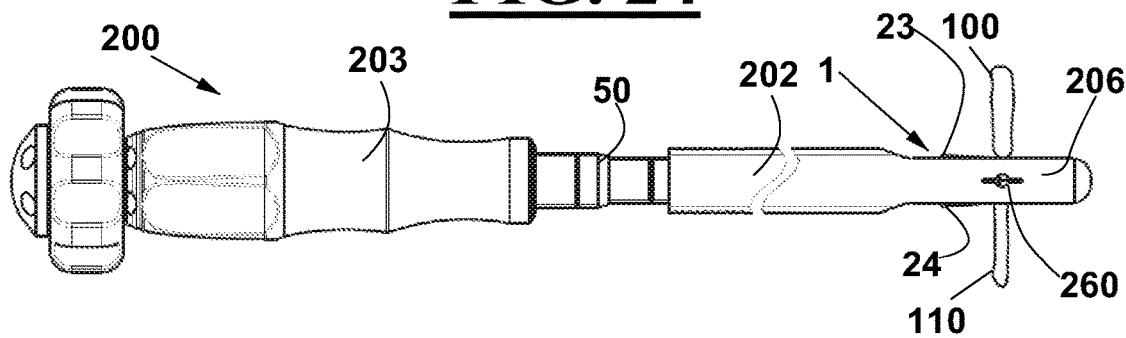

With reference to FIGS. 22-24, subsequent conditions are depicted of a step of introducing a fusion device, providing the introduction, in particular with the fusion device 1 according to the invention, but also with similar devices or equivalent, in the interspinous space through the introduction tube of FIG. 21.

Figure 25:
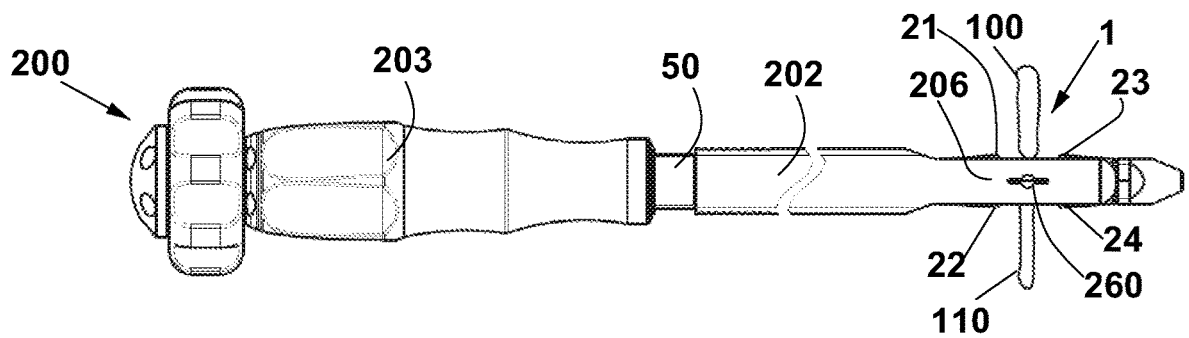
FIGS. 25-27 show subsequent conditions of a step of opening the jaws of a fusion device and of locking the intervertebral fusion device according to the invention on the spinous apophysis, to obtain a positioning as shown in FIGS. 22-24.
Figure 26:
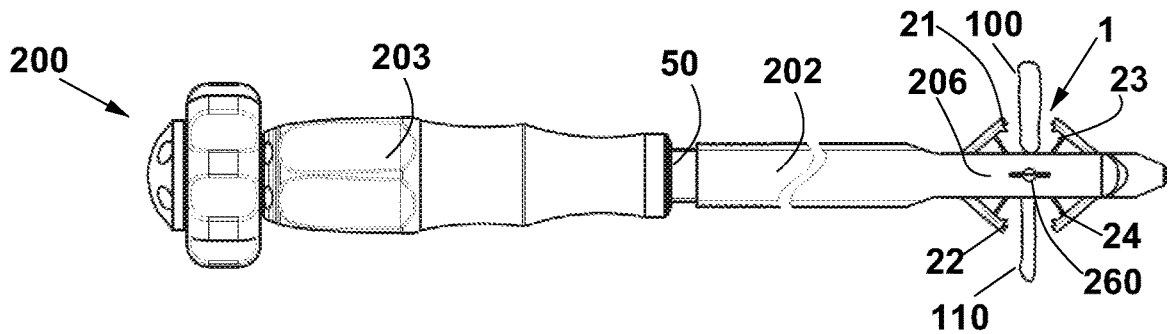
Figure 27:
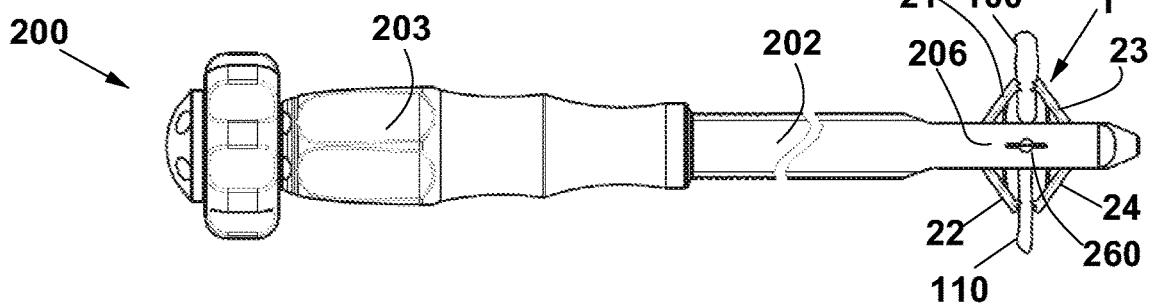

With reference to FIGS. 25-27 are shown subsequent conditions of a step of opening the jaws and of locking on the spinous apophyses of an intervertebral fusion device according to the invention located as in FIGS. 22-24, similar to the steps of FIG. 6A-6F.

The foregoing description some exemplary specific embodiments will so fully reveal the invention according to the conceptual point of view, so that others, by applying current knowledge, will be able to modify and/or adapt in various applications the specific exemplary embodiments without further research and without parting from the invention, and, accordingly, it is meant that such adaptations and modifications will have to be considered as equivalent to the specific embodiments. The means and the materials to realize the different functions described herein could have a different nature without, for this reason, departing from the field of the invention. It is to be understood that the phraseology or terminology that is employed herein is for the purpose of description and not of limitation.

The invention claimed is:

1. An interspinous fusion device comprising:
   a central body defining a longitudinal direction and configured to be inserted between two adjacent spinous processes;
   a proximal body and a distal body, opposite to each other with respect to said central body configured to translate towards each other along said longitudinal direction;
   a pair of proximal jaws and a pair of distal jaws opposite to each other with respect to said central body, spaced apart from each other along said longitudinal direction, and having a first end connected by hinge to said proximal body and to said distal body, and a second end configured to abut against said spinous processes;
   an actuation system of said proximal and distal bodies, configured to be percutaneously actuated to cause said relative translation and to cause a rotation of said jaws about said proximal and distal bodies, so that said jaws perform a displacement from a closed configuration to an open configuration; and
   connecting rods that connect said central body to said pair of proximal jaws and said pair of distal jaws, said connecting rods having a first hinge point on said central body and a second hinge point at respective intermediate hinges of said jaws;
   wherein:
   said second ends, in said closed configuration of said jaws, are arranged at a first distance from said first hinge points and at a second distance from said intermediate hinges, respectively, and
   said first distance is shorter than said second distance, such that, when said jaws move from said closed configuration to said open configuration, said second ends move substantially transversally to said longitudinal axis and minimize the entrapment of biological tissues between the second ends of the jaws and said spinous processes.

2. The interspinous fusion device according to claim 1, wherein said first distance is shorter than 5 mm.

3. The interspinous fusion device according to claim 1, said actuation system comprising:
   a threaded shaft configured to rotate about said longitudinal direction, said threaded shaft comprising, at a first end, a head associated with said proximal body and, at a second end, and comprising a distal nut element that is associated with said distal body and is arranged to engage with said second end of said threaded shaft, said head and said distal nut element and distal bodies, respectively, forces that are parallel to said longitudinal direction and have opposite directions directed towards said central body, in order to cause said relative translation of said distal body towards said proximal body by a rotation of said threaded shaft.

4. The interspinous fusion device according to claim 3, wherein said distal nut element that is associated with said distal body is selected from the group consisting of:
   a nut element external to said distal body with respect to said central body;
   a nut element comprising a flange portion with respect to said central body, comprising an extension portion having a nut portion arranged to engage with said threaded shaft, said extension portion having substantially a same length as the translation length of said threaded shaft when passing from said closed configuration to said open configuration of said jaws;
   a nut element integrated in said distal body; and
   a nut element integrated in said distal body comprising an extension portion having a nut portion arranged to engage with said threaded shaft, said extension portion having substantially a same length as the translation length of said threaded shaft when passing from said closed configuration to said open configuration of said jaws.

5. The interspinous fusion device according to claim 4, wherein said threaded shaft comprises a first threaded portion configured to engage with said central nut element, a second threaded portion configured to engage with said distal nut element, said first and second threaded portions having a ratio between the respective thread pitches equal to 1:2.

6. The interspinous fusion device according to claim 1, wherein said actuation system comprises a threaded shaft, configured to rotate about said longitudinal direction, said distal body associated with a distal nut element, said central body associated with a central nut element, said distal and central nut elements configured to translate along said longitudinal direction and to cause said jaws to perform said displacement from said closed configuration to said open configuration by a rotation of said threaded shaft.

7. The interspinous fusion device according to claim 1, wherein said hinges and said first hinge points and said second hinge points are plastic constraints made of portions of foldable material.

8. The interspinous fusion device according to claim 1, wherein said proximal, distal and central bodies are tubular bodies.

9. The interspinous fusion device according to claim 1, wherein said central body, said proximal body, said distal body, said connecting rods and said proximal and distal jaws are two symmetrical halves configured to be connected along a longitudinal plane containing said longitudinal direction.

10. The interspinous fusion device according to claim 1, wherein said connecting rods have a length substantially equal to the distance between said second hinge point of said jaws and said second end of said jaws.

11. The interspinous fusion device according to claim 1, wherein said actuation system comprises a tie-rod element having an end configured to engage with said distal body, said tie-rod element configured to be pulled so as to pull in turn said distal body towards said central and proximal bodies.

12. The interspinous fusion device according to claim 1, wherein said proximal body, said central body and said distal body have a rectangular cross section.

13. The interspinous fusion device according to claim 1, wherein said jaws are configured to move from said closed configuration to said open configuration in a predetermined fusion plane containing said longitudinal direction.

14. A system of an interspinous fusion device and an introduction device, said interspinous fusion device comprising:
    a central body defining a longitudinal direction and configured to be inserted between adjacent spinous processes;
    a pair of proximal jaws and a pair of distal jaws that are opposite to each other with respect to said central body and are spaced apart from each other along said longitudinal direction; and
    an actuation system of said proximal jaws and of said distal jaws, configured to be percutaneously actuated in such a way to move said jaws from a closed configuration to an open configuration of said jaws, wherein, in said open configuration, said jaws have free ends abutting against said spinous processes;
    wherein:
        said jaws are configured to move from said closed configuration to said open configuration in a predetermined fusion plane containing said longitudinal direction;
        said introduction device comprises an introduction tube configured to be inserted between two spinous processes, said introduction tube comprising a distal end, said introduction tube configured to guide said interspinous fusion device until said interspinous fusion device protrudes from said distal end of said introduction tube, and
        said introduction tube comprises two stiff wings extending from said distal end, said stiff wings oriented in such a way that, when said interspinous fusion device protrudes from said distal end, said interspinous fusion device can be freely moved from said closed configuration to said open configuration in a predetermined fusion plane containing said longitudinal direction, and said stiff wings are arranged parallel to said predetermined fusion plane,
        wherein said stiff wings have a predetermined width, and said central body has a predetermined height in said fusion plane, said width of said stiff wings substantially equal to said height of said central body, such that said stiff wings work as a spacer between two adjacent spinous processes when said interspinous fusion device is caused to protrude from said distal end, and
    said system also comprising a file tool arranged to be slidingly received within said introduction tube and to protrude between said two stiff wings so as to form a passageway for said interspinous device through biological tissues.

15. The system of an interspinous fusion device and an introduction device according to claim 14, wherein:
    at least said central body of said interspinous fusion device has a rectangular cross section, and
    said introduction tube has a rectangular cross section configured to slidingly guide said interspinous fusion device.

16. The system of an interspinous fusion device and an introduction device according to claim 15, wherein:
    said file tool has a rectangular cross section, and
    wherein a first pair of opposite faces of said file tool comprises abrasive surfaces, whereas a second pair of opposite faces of said file tool.

17. The system of an interspinous fusion device and an introduction device according to claim 14, wherein said central body of said interspinous fusion device has a marker, and at least one of said stiff wings of said introduction tube has a hole, said hole arranged in such a way that, when said interspinous fusion device completely protrudes from said distal end, said marker and said hole are aligned and said marker is visible to an imaging apparatus through said hole.

18. The system of an interspinous fusion device and an introduction device according to claim 14, wherein:
    said file tool has a rectangular cross section, and
    a first pair of opposite faces of said file tool comprises abrasive surfaces, whereas a second pair of opposite faces of said file tool comprises smooth surfaces.

* * * * *